United States Patent [19]

Paavola et al.

[11] Patent Number: 4,473,080
[45] Date of Patent: Sep. 25, 1984

[54] BLOOD PRESSURE INSTRUMENT

[76] Inventors: Oiva A. Paavola, 3024 W. 26th St., Erie, Pa. 16506; Neal Fearnot, 832 Ashland St., W. LaFayette, Ind. 47906

[21] Appl. No.: 334,170

[22] Filed: Dec. 24, 1981

[51] Int. Cl.³ ............................................... A61B 5/02
[52] U.S. Cl. .................................................... 128/678
[58] Field of Search ................. 128/672, 678, 687–690

[56] References Cited

U.S. PATENT DOCUMENTS

| 2,753,863 | 7/1956 | Bailey ................................. | 128/680 |
| 3,704,708 | 12/1972 | Iberall ............................... | 128/680 |
| 3,811,429 | 5/1974 | Fletcher et al. ..................... | 128/687 |
| 4,068,654 | 1/1978 | Paavola et al. ..................... | 128/689 X |
| 4,188,955 | 2/1980 | Sakamoto et al. .................. | 128/680 |
| 4,295,471 | 10/1981 | Kaspari .............................. | 128/687 X |

FOREIGN PATENT DOCUMENTS 7710933 10/1977 Netherlands ....................... 128/689

Primary Examiner—Kyle L. Howell
Assistant Examiner—F. J. Jaworski
Attorney, Agent, or Firm—Charles L. Lovercheck; Wayne L. Lovercheck; Dale R. Lovercheck

[57] ABSTRACT

An instrument for measuring blood pressure by sensing the Korotkoff sounds which prevail only between the systolic and diastolic point. The instrument used is essentially a hand-held device. The instrument has a pressure-sensitive element made up of a flexible material containing fluid and crystal transducer supported on the flexible material which responds to the Korotkoff sounds. The sensor is made in a unique geometrical structure shaped to fit between bones and tendons over an artery. The crystal operates through an amplifier, a high pass filter and low pass filter through a comparator to a one shot enabling means connected to a panel meter. The pressure on the fluid in the sensed by a pressure sensor that is in contact with the fluid in the sensor which is connected to the panel digital meter. The digital display shows the pressure exerted on the artery at each Korotkoff sound. A LED shows that pulses are present. The pressure sensed by the pressure transducer at the time the sounds appear at the systolic point and again at the time they disappear at the diastolic point.

1 Claim, 4 Drawing Figures

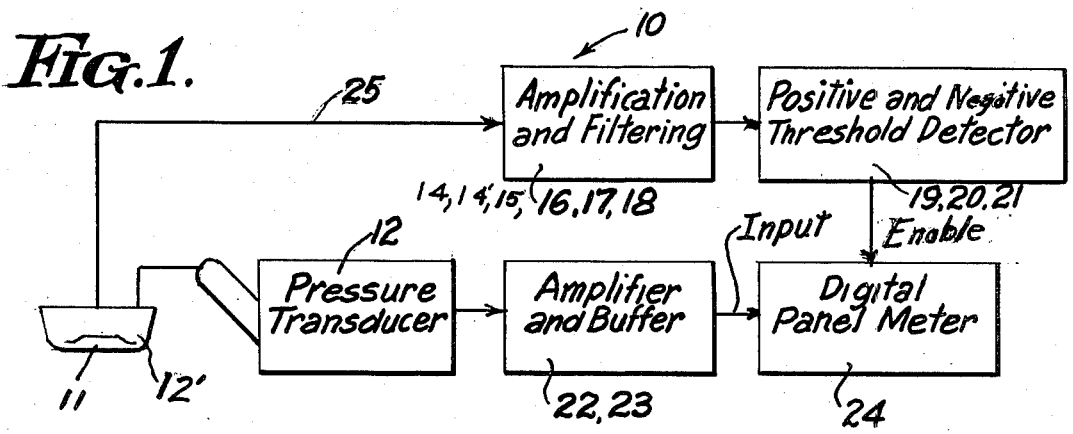
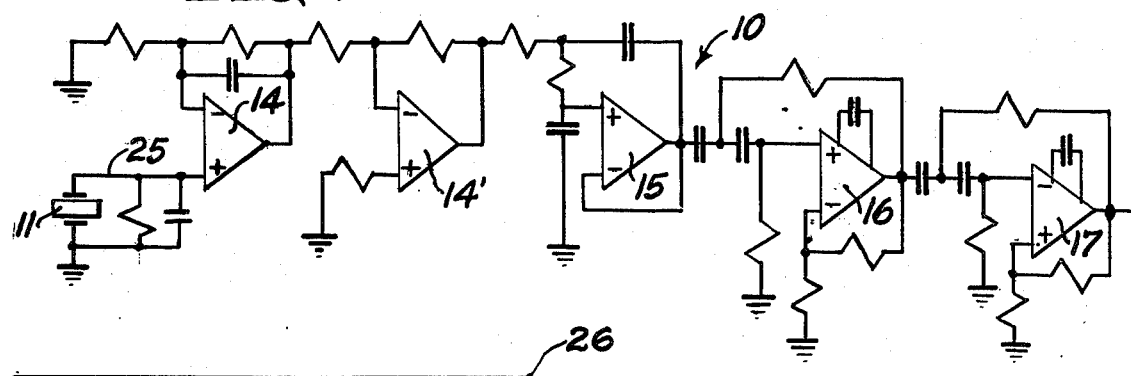
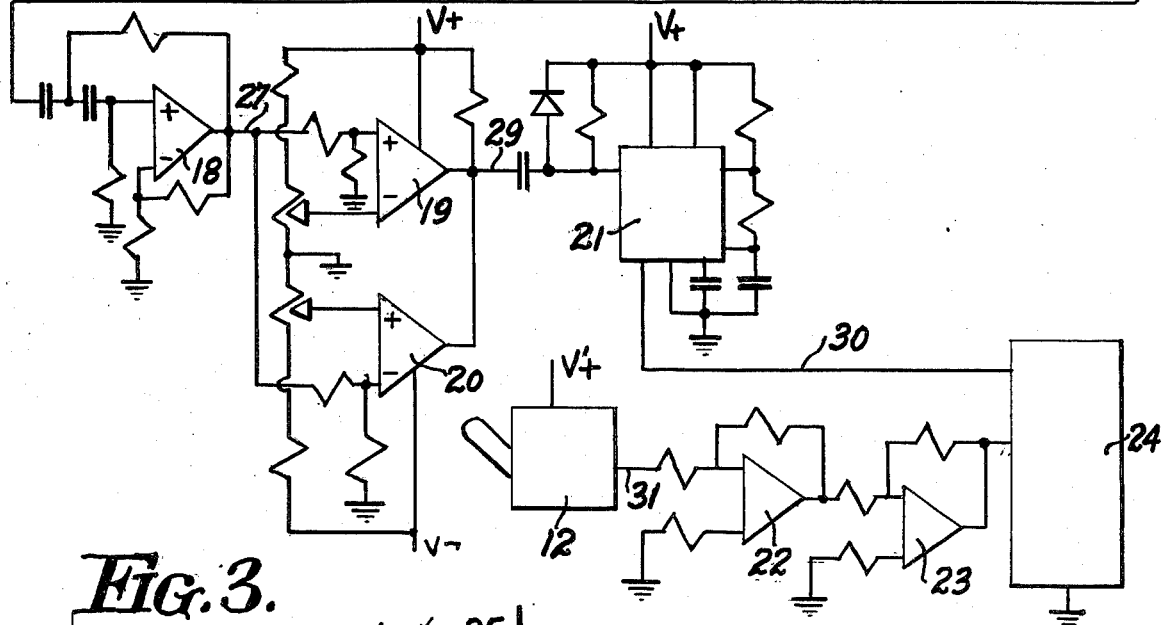
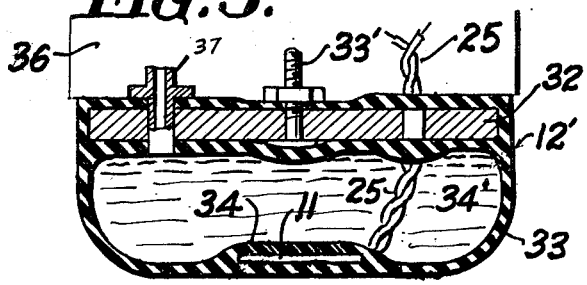
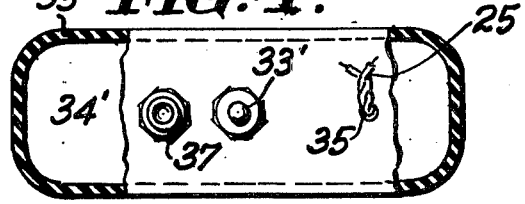

BLOOD PRESSURE INSTRUMENT

REFERENCE TO PRIOR ART

Related U.S. petents are: U.S. Pat. Nos. 3,814,083; 3,930,494; 3,807,388; 3,123,068; 3,773,038; 3,742,937; 3,572,316; 3,230,950; 1,802,685; 1,900,285; 3,623,476.

Related foreign Patents are: German No. 509,637; German No. 469,703.

BACKGROUND OF THE INVENTION

A. The need for band pass charateristics of the Korotkoff sound amplifier. Since the radial (or brachial) pulse has frequency components extending into the audible range, it can be confused with Korotkoff sounds. The sounds from the radial pulse are present from systolic pressure to far below diastolic. Korotkoff sounds are only present when the artery is partially occluded with a pressure between systolic and diastolic pressures. Therefore, for accurate (or even repeatable) measurements of diastolic pressure, stringent requirements exist on the low frequency cutoff of the band pass filter.

Noise from movement occurs in the brachial cuff but is less apparent in our device because of the small area and soft material interface with the skin. Nevertheless, a high frequency cutoff is desired to reduce the noise from movement, muscle tremor, etc. Hence, a band pass filter (not only low pass or high pass) is required to obtain both systolic and diastolic pressure.

B. Korotkoffs' sounds, unlike radial pulses, can be muffled or disappear between systolic or diastolic. There are two reasons that this may occur. One is called the ausculatory gap. Of the five stages of the Korotkoff sounds produced by reducing the pressure from above systolic to below diastolic, the middle stage, in some people is faint and even non-existent due to the characteristics of the blood vessel. The second cause of the muffling Korotkoffs' sounds is venous pooling generally caused in a cuff method by the inflating the cuff too slowly. Because the pressure in the venous system is less than in the arterial system, the cuff occludes the veins first and blood continues to flow in the artery, but not in the veins at cuff pressure between venous and arterial pressure.

The pressure of venous pooling causes the sounds to be altered, sometimes causing them to cease early and sometimes causing them to extend above systolic and below diastolic down to venous pressure (about 5–10 mmHg.). One advantage of our system over the cuff is that it cannot create venous pooling since a whole member is not occluded and therefore, it eliminates this complication.

It is an object of the invention not to be confused by an ausculatory gap. Devices which provide a time window in which the next Korotkoff sounds are to occur are often fooled by the ausculatory gap and therefore provide inaccurate pressure measurement.

C. It is important to establish the reliability of the pressure measurement on each person. It is well known, for instance, that measurement with a cuff on two people with equal blood pressures will be very different if the arm circumference of the two people is different. Instead, to be most accurate, the cuff width must be proportioned to the arm circumference. Similarly, it is the object of this invention to provide an indication of the reliability of the measured pressure. Unlike prior art, this invention does provide an indication of reliability. From the signal picked up by the sound sensing means, two signals arise. (1) Korotkoffs sounds are obtained by filtering as previously described, and (2) sounds arising from the pulse of blood, passing beneath the sensor, are obtained for the purpose of establishing the reliability of the measurements.

Korotkoff sounds are used to determine the systolic pressure and the diastolic pressure. Displaying pressure at each occurrence of Korotkoff sounds indicates to the user the rate at which the user is allowing the pressure to drop. Different from these two purposes, the Korotkoff sounds indicate the pressure of the auscultatory gap, if present. Hence, one of the objects of this invention is to use Korotkoff sounds for the above three purposes in combination. Separate from the above object it is the object of our invention to use sounds obtained from an underlying arterial pulse, these sounds not being Korotkoffs sounds, and these sounds indicating the presence of an underlying artery. It is well known that sounds are produced by an artery and that these sounds exist when an artery is partially occluded, and may extend to pressures far below diastolic. If these sounds are detected when our device is placed in position on the skin then we have an indication that Korotkoff sounds obtained from the same sensor will be reliable. To provide this reliability signal an LED indicator, easily visible to the operator, indicates whether a pulse is being sensed beneath the sensor. Since this pulse can be sensed above systolic and below diastolic, it is different from sensing only Korotkoff sounds. When a pulse is sensed beneath the sensor the operator will see the LED flashing with each pulse and will be able to rely on the obtained pressures. This feature is a significant advantage over the prior arts since prior art has no indication of sensor position with respect to underlying arteries separate from, yet in conjunction with Korotkoff sounds. The greatest advantage is in the measurement of diastolic pressure where it is well known that Korotkoff sounds do not cease abruptly. The amplitude of Korotkoff sounds is related to the distance between the artery and the sensor and therefore, it is related to sensor position if the sensor is not centered over the artery. If the sensor is not centered over the artery, Korotkoff sounds may attenuate too early and the resulting diastolic pressure will be too high. It is an advantage and an object of the device to guard against this error.

D. The geometric shape and materials used in the sensing device are of an advantageous nature. In prior art little, if any, attention has been given to the shape or material of the sensor. Since this device senses both the pulse and Korotkoff sounds, the shape and materials are novel constructions. One object of this invention is a sensor that is optimally suited for application over an artery. The sensor is long enough to occlude a significant portion of an artery, enough to obtain blood pressures, yet not occlude too much making the occlusion force greater than can be applied by hand. The width of the sensor is less than its lenth to allow the sensor to penetrate between tendons, bones, and other obstructing structures. For example, blood pressure can be obtained from the radial artery because this geometry will occlude the artery against underlying bone and penetrate between the radial projection and the contractor tendons of the forearm. This unique geometry allows blood pressure to be taken at many points in the body where an exposed artery is present. Many times an artery is protected by adjacent structures making blood pressure obtained with prior art inaccurate or impossible. The sensor of this invention has a pliable membrane conformable to anatomical structures with a geometric shape of rectangular with rounded corners. This unique combination allows the measuring of blood pressure at locations that are easily accessible and that the prior art has not been able to take advantage of them.

GENERAL DESCRIPTION OF THE INVENTION

Most prior art patents are applicable only with the standard Riva-Rocci-Korotkoff ausculatory method using a cuff to occlude a member. This method requires that applied pressure be decreasing as measurements are taken resulting in only one measurement of each systolic and diasotlic pressure per procedure. Prior art patents disclosing devices that obtain blood pressure using a sound sensing means but no occlusion cuff exhibit inherent difficulties and yield less accurate results.

The blood pressure instrument disclosed in the present application has advantages over prior art that were not disclosed or suggested in the spirit of the prior art.

The blood pressure instrument including the electricl circuit, including the LED which indicates when the sensor is in position over an artery, including the rigid frame supporting the circuit and diaphragm which will be insertable over an artery in relatively inaccessible locations described hereinafter exhibit the following advantages over the prior art:

1. A simpler device and simpler circuit providing the ability to obtain more accurate measurements of critical blood pressures by allowing the operator to deviate from the standard ausculatory method and by allowing the operator to measure systolic and diastolic pressures by both increasing and decreasing applied pressure and thereby repeatedly occluding and unoccluding an artery in order to obtain several almost simultaneous readings of systolic pressure thereby obtaining a more accurate systolic pressure measurement, and by repeatedly decreasing applied pressure to observe cessation of Korotkoff sounds and reapplying pressure until reappearance of Korotkoff sounds and repeating this procedure to obtain several almost simultaneous measurements of diastolic pressure thereby obtaining a more accurate diastolic pressure measurement.

2. A device that contains the essential circuitry to allow blood pressures to be measured as described above requiring an indicator of the change in applied pressure between heart beats, an indicator of the presence or absence of Korotkoff sounds, an appropriate bandpass filter with both upper and lower cutoff frequencies excluding environmental noise and noise created by the operator arising from performing the procedure as described above, electronic circuitry allowing repeated almost simultaneous measurements of the pressure of interest while either increasing of decreasing pressure beginning at any initial pressure, an indicator or applied pressure of each appearance of Korotkoff sounds, a sensing mechanism that does not require occlusion of a major portion of the blood supply to a limb and is adapted to occluding arteries between muscles, tendons and other anatomical structures, that monitors sensitively Korotkoff sounds and the applied pressure.

3. A device that is simple and compact enough to be miniaturized and yet contains all the essential required components in combination as described above to allow measurement of blood pressures by the method described above, thereby obtaining more accurate measurements.

4. A device that allows the operator to detect an ausculatory gap, or silent interval when Korotkoff sounds don't exist that occurs in some people between systolic and diastolic pressures, without obtaining incorrect measurements of systolic or diastolic pressures.

Furthermore, the applicants' circuit is far simpler, more economical to build and reliable than the circuits of the references.

OBJECTS OF THE INVENTION

It is an object of the invention to provide an improved device for indicating blood pressure.

It is another object of the invention to provide blood pressure instrument indicating pressures at systolic and diastolic pressures that will not be confused by the ausculatory gap.

Another object of the invention is to provide a device for indicating blood pressure which is simple in construction, economical to manufacture, and simple and efficient to use.

Another object of the invention is to provide a blood pressure measuring device wherein a crystal senses Korotkoff sounds and the pressure is sensed by a strain gage. Information from the crystal and the strain gage are converted to a digital reading of the applied pressure at each heart beat between the limits of the systolic and diastolic pressures.

Another object is to provide a digital readout on a blood pressure instrument wherein an LED indicates that the Korotkoff sound sensor is over an underlying artery.

With the above and other objects in view, the preent invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

GENERAL DESCRIPTION OF THE DRAWINGS

FIG. 1 is a block diagram of the circuit according to the invention.

FIG. 2 is a schematic diagram of the circuit for carrying out the invention.

FIG. 3 is a longitudinal cross-sectional view of the transducer.

FIG. 4 is a top view of the transducer shown in FIG. 3.

DETAILED DESCRIPTION OF THE DRAWINGS

Now, with more particular reference to the drawings, the circuit is generally shown in FIG. 2 wherein a crystal element 11 is supported on the flexible diaphragm of the transducer 12'. The crystal element 11 is connected to the input amplifier 14 by the line 25 and input amplifier 14 is connected to the gain amplifier 14' then to the high pass filter of the second order 15 and to the sixth order low pass filter to include 16, 17, and 18, thence through the line 27 to the comparators 19 and 20 for positive and negative threshold detection to the one shot 21 for enabling panel meter that in turn is connected through the line 30 to the digital panel meter 24.

One shot 21 is a (LM 555) monostable multivibrator which is common to anyone skilled in the art. Pressure transducer 12 could be (LX1602-G) pressure gage or a pressure transducer of the LX 16/17 series by National Semiconductor.

Digital Panel Meter (DPM)24 converts an analog signal to a digital signal for the purpose of displaying the value of the analog signal on a digital readout. The conversion and display are to be enabled by line 30 so that upon receiving an enable pulse from the one shot the conversion will be enabled as will the display.

The pressure transducer 12 is connected through the line 31 to the amplifiers 22 and 23 which are in turn connected to the digital panel meter 24.

The circuit components including resistors and capacitors are of a type familiar to those skilled in the art.

The block diagram shown in FIG. 1 shows the sound microphone 11 connected to line 25 to the amplification and filter members 10 to the positive and negative threshold detector 19 and 20 and to one shot 21, thence to the digital panel meter 24 which is in turn connected to the buffer and amplifier 22 and 23 to the pressure transducer. Positive and negative threshold detector 13 is connected to LED 13'. Microphone 11, amplifiers 14, 14', 15, 16, 17, and 18, threshold detectors 19 and 20 and one shot 21 can be considered to be a second circuit. Elements 12, 22, 23, and 24 can be considered a first circuit. The signal processing circuit may be housed in the handle 36 of the apparatus.

The transducer shown in FIGS. 3 and 4 in detail has the aluminum rigid frame 37 which may be mounted to a suitable hand-held instrument by means of the mounting hardware 33' which may be a suitable stud, screw and nut or the like. The molded silicone rubber diaphragm 33 is cemented or otherwise attached to the frame 32 and has a space 34' therein which contains a hydraulic fluid or gas. The crystal element 11 is bonded to the inside of the flexible material of the container 33 by a suitable flexible adhesive material indicated at 34. The lines 25 connect the crystal to the input amplifier 14. The wire extends to a sealed exit hole 37 which seals the fluid or gas in the space 34' against leakage. The pressure transducer 12 may be connected in fluid flow relation with the fluid in the space 34' by member 37. The dimension of the transducer should be about two (2) centimeters long by one (1) centimeter wide by one (1) centimeter high. The bored member 37 may be used to connect the fluid in space 34' with the pressure transducer 12'.

A person using the device may hold the handle 36 in his hand and bring the flexible diaphragm 33 into engagement with the skin of the person whose blood pressure is to be analyzed and apply pressure to the handle 36 thereby exerting pressure on the skin sufficient to occlude the artery. The light LED will commense to flash as soon as the diaphragm rests on an artery and the LED continues to flash until the pulse is stopped or until the diaphragm moves off the artery. When the pressure is gradually decreased until Korotkoff sounds appear, the microphone crystal 11 will sense these sounds and these sounds will trigger the one shot 21 enabling digital panel meter 24 to read out the pressure exerted on the fluid or gas in space 34' which is the pressure at the systolic point. Pressure will continue to be displayed upon sensin Korotkoff sounds until the diastolic point is reached after which pressure the crystal 11 will no longer sense Korotkoff sounds.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. An instrument for measuring blood pressure comprising, an electronic circuit,
   pressure sensing means having handle means thereon for holding in the hand of a person,
   a sensor attached to said handle means,
   said sensor comprising pressure sensing means including a flexible diaphragm adapted to be held in contact with the skin of a body and to be forced against said skin applying pressure whereby an artery under said skin is occluded substantially stopping the flow of blood through said artery.
   said sensor being about one centimeter wide, two centimeters long and one centimeter high and adapted to be disposed over arteries on inaccesible areas,
   said diaphragm having crystal molded in said diaphragm adapted to detect Korotkoff sounds and pulses of blood in said artery,
   said pressure sensing means connected to said diaphragm and digital readout means being adapted to read the pressure exerted on said artery at each of said Korotkoff sounds,
   second circuit means permanently connecting said crystal to said digital readout,
   said second circuit means permanently connecting said pressure sensing means to said digital readout comprising an amplification and filtering means including a band pass filter to filter out extraneous noises from affecting said readout and a high pass filter and a low pass filter out frequencies below the frequency of Korotkoff sounds and high frequency sounds above the frequency of Korotkoff sounds thereby filtering out extraneous noises,
   a first positive and negative threshold detetor connected between said amplification and filtering means,
   a LED connected to said amplification and filtering means for indicating when said sensor is over an artery.

* * * * *